United States Patent [19]
Morris

[11] Patent Number: 6,024,719
[45] Date of Patent: Feb. 15, 2000

[54] METHOD AND APPARATUS FOR PERFORMING SURGERY INSIDE THE HUMAN RETINA USING FLUIDIC INTERNAL LIMITING MEMBRANE (ILM) SEPERATION (FILMS)

[76] Inventor: Robert E Morris, 3204 Argyle Rd., Birmingham, Ala. 35213

[21] Appl. No.: 09/111,146

[22] Filed: Jul. 6, 1998

[51] Int. Cl.$^7$ ............................ A61M 1/00; A61M 31/00
[52] U.S. Cl. ............................................. 604/28; 604/521
[58] Field of Search ........................... 604/28, 294, 506, 604/521, 890.1

[56] References Cited

U.S. PATENT DOCUMENTS

| | | | |
|---|---|---|---|
| 5,037,384 | 8/1991 | Chang | 604/521 |
| 5,066,276 | 11/1991 | Wang | 604/521 |
| 5,476,511 | 12/1995 | Gwon et al. | 604/890.1 |
| 5,616,122 | 4/1997 | Lam et al. | 604/521 |
| 5,697,898 | 12/1997 | Devine | 604/22 |
| 5,722,428 | 3/1998 | Kaplan et al. | 604/506 |
| 5,725,493 | 3/1998 | Avery et al. | 604/294 |
| 5,766,242 | 6/1998 | Wong et al. | 604/890.1 |
| 5,817,075 | 10/1998 | Giungo | 604/294 |
| 5,830,173 | 11/1998 | Avery et al. | 604/294 |

OTHER PUBLICATIONS

Trese, M. et al., "Macular pucker Ultrastructure," *Graefe's Arch Clin Exp Ophthamol.* (1983) 221:16–26.

De Bustros, S. et al., "Vitrectomy for Macular Pucker: Use After Treatment of Retinal Tears of Retinal Detachment," *Arch Ophthalmol.* (1988) 106:758–760.

Sivalingam, A. et al., "Visual Prognosis Correlated with The Presence of Internal Limiting Membrane in Histophathologic Specimens Obtained from Epiretinal Membrane Surgery," *Ophthalmology.* (1990) 97:1549–1552.

Brooks, H.L., "ILM Peeling in Full Thickness Macular Hole Surgery," *Vitreoretinal Surgery and Technology*, (1995) 7:2.

Rice, T.A., "Technique of Removal of the Inner Retinal Surface In Macular Hole Surgery," *Retina Society 28$^{th}$ Annual Meeting*, Santa Fe, New Mexico, 1995.

Morris, R., et al. "Internal Limiting Membrane (ILM) Maculorrhexis for Traction Maculopathy," *Vitreoretinal Surgery and Technology* (1997) 8(4):1.

Morris, R. et al., "Hemorrhagic Macular Cysts in Terson's Syndrome and Its Implications for Macular Surgery", *Developments in Opthalmology* (1977) 29:44.

Morris, R., et al.., "Retinal Folds in Terson Syndrome," *Ophthalmology* (1994) 101:1.

*Primary Examiner*—Wynn Wood Coggins
*Assistant Examiner*—Jennifer R. Sadula
*Attorney, Agent, or Firm*—Lyon & Lyon LLP

[57] ABSTRACT

A method and apparatus for performing surgery inside the human retina using fluidic internal limiting membrane separation (FILMS) to remove the internal limiting retinal layer from the neural retinal layer at the macula. The method comprises inserting a hollow microcannula between the retinal internal limiting membrane and the neural retinal layer at or near the macula and injecting a sterile fluid, such as sodium hyaluronate, through said microcannula and thereby raising the macular internal limiting membrane retinal layer away from the neural retina such that it can then be removed by conventional means, while simultaneously smoothing the neural retina by localized pressure tamponad. The apparatus comprises a hollow microcannula having a proximal end a distal end and a distal tip. The distal end is shaped to conform tangentially to the surface of the retina. The distal tip is sharply beveled and adapted to discharge a fluid substance and to easily insert under the internal limiting membrane retinal layer and achieve occlusion of the lumen upon minimal insertion, and is sufficiently microscopic as to not substantially injure the neural retina when introduced under the ILM.

6 Claims, 3 Drawing Sheets

METHOD AND APPARATUS FOR PERFORMING SURGERY INSIDE THE HUMAN RETINA USING FLUIDIC INTERNAL LIMITING MEMBRANE (ILM) SEPERATION (FILMS)

BACKGROUND OF THE INVENTION

1. Field of the Invention

The present invention is directed generally to medical procedures and, more particularly to a medical procedure for removal of the innermost layer of the human retina (internal limiting membrane) from the underlying neural retina at the center of vision (macula).

2. Background Art

The rays of light entering the eye (FIG. 1) and bearing the pattern of the object being looked upon pass through the cornea 32, the aqueous humor, the pupil, the lens 34, and the vitreous humor, then fall upon the retina 26. The retina is the light sensitive film lining the back two-thirds of the eye. Its appearance is similar to that of wet tissue paper. Its layers consist of the internal limiting membrane (ILM), the neurosensory retina, and the retinal pigment epithelium; the ILM, being innermost, is the retinal border with the vitreous gel cavity 42. If the parts of the eye are normal and the lens is properly adjusted, the image will be focused upon the retina. This condition results in clear vision. At the back of the eye or, more specifically, the back part of the retina is the macula lutea 36 having at its center the fovea centralis. The macula is a small orange-yellow, oval area (about 3 mm by 5 mm) of the retina adjacent to the optic nerve 38. Vision in which the image of the object looked upon falls upon the macula is the sharpest vision and is called macular vision or central vision, as opposed to gross, peripheral vision.

A wrinkling of the internal limiting membrane and the neural retina is called macular pucker. This can cause loss of fine vision to the level of legal blindness. The wrinkling is caused by contractile cells or fibrocellular membranes (epimacular proliferation or EMP) and is usually a process associated with aging.

Macular distortion and macular edema, with resultant macular dysfunction, are recognized sequelae of EMP. Often, the macula will have a "wrinkled cellophane" appearance. According to one theory, this appearance represents internal limiting membrane (ILM) distortion by surface proliferative cells without a distinct epimacular proliferative membrane overlying the ILM, which might be surgically removed. This ILM cellophaning may persist or occur months after seemingly successful removal of EMP, limiting visual recovery.

Specimens analyzed after vitrectomy (the surgical removal of a portion of the vitreous body and/or associated epiretinal or fibrous membranes) using a microscope for epimacular membrane removal often contain retinal ILM fragments that have been intentionally or unintentionally removed to treat "traction maculopathy," a term introduced by Morris, R., Kuhn, F., Witherspoon, C. D., ("Retinal folds and hemorrhagic macular cysts in Terson's syndrome," *Ophthalmology* (1994) 101:1). Written reports differ on whether the presence of ILM fragments correlate with the visual outcome. (Trese, M. et al., "Macular pucker Ultrastructure," *Graefe's Arch Clin Exp Ophthamol.* (1983) 221:16–26; De Bustros, S. et al., "Vitrectomy for Macular Pucker: Use after treatment of retinal tears or retinal detachment," *Arch Ophthalmol.* (1988) 106:758–760; Sivalingam, A. et al., "Visual prognosis correlated with the presence of internal limiting membrane in histophathologic specimens obtained from epiretinal membrane surgery," *Ophthalmology.* (1990) 97:1549–1552). More recently, William Hutton and others have implicated even relatively small amounts of traction as exacerbating diabetic macular edema.

Additionally, Logan Brooks and Tom Rice have advocated the intentional removal of the macular ILM in macular hole surgery. (Brooks, L., "ILM peeling in full thickness macular hole surgery," Vitreoretinal Surgery and Technology. (1995) 7:2; Rice, T. A., "Technique of removal of the inner retinal surface in macular hole surgery," *Retina Society 28th Annual Meeting.* Santa Fe, N.Mex., 1995). A macular hole is thought to occur as a result of tangential traction on the retina at the macula, usually leading to legal blindness Thus, there are many advocates of the importance of ILM removal in macular hole surgery. Previous methods as shown in FIG. 2, developed over a period of about twenty years, have removed the macular ILM 54 and EMP 50 utilizing the manual, mechanical method with grasping forceps 52. This forceps procedure is the most delicate surgical maneuver performed on the human body. The procedure requires ideal surgical conditions and expert skill. Ideally, cataracts and any other opacity obscuring surgical view will have been eliminated for safe and predictable EMP/ILM removal. Electron microscopy of surgical specimens frequently demonstrates cellular proliferation contracting the ILM. It is believed that the increased mobility of an ILM denuded macula contributes to successful hole closure.

Furthermore, the results with ILM maculorhexis in macular hole surgery were encouraging. In a consecutive series of 32 idiopathic holes with less than two years duration, a 97% closure was achieved. Previous macular hole edges were rarely discernible. Visual acuity improved at least two Snellen lines in 91% of eyes, and 41% of eyes achieved 20/40 or better visual acuity at the last follow-up (Morris, R., Witherspoon, C. D., "Internal Limiting Membrane Maculorhexis for Traction Maculopathy," *Vitreoretinal Surgery and Technology* (1997) 8(4):1).

All of the above-described conditions may be considered forms of traction maculopathy as first described by Morris et al. The ultimate goal of all surgery to cure traction maculopathy is to return the neural retina to its normally smooth contour, allowing resumption of fine vision and relief from distorted vision.

In a very rare disease called Terson's syndrome, blood under pressure from a ruptured vein or capillary spontaneously lifts the ILM, resulting in what is called a hemorrhagic macular cyst (HMC) (Morris, R., Kuhn, F., Witherspoon, C. D., American Academy of Opthalmology, 1990). The hemorrhage usually then breaks through the ILM into the vitreous. Vitreous and subinternal limiting membrane hemorrhage occurs as a result of abrupt intracranial hemorrhage from an aneurysm or closed head trauma. Although the exact mechanism for these hemorrhages is unknown, it is thought that the sudden increased intracranial pressure is transmitted via the optic nerve to retinal venules and capillaries, rupturing them. If bleeding has occurred at the macula, it will appear as a circular or boat shaped cyst (HMC) on the surface of the retina. The HMC is usually encircling the macula. Its diameter and height vary, as does its color, depending on the longevity of the hemorrhage. Early intervention (i.e., for amblyopia prevention in infants) finds a reddish cyst. A few months after the incident, the surgeon encounters a yellow lesion (degenerated blood products), a clear membrane spanning an optically empty cavity, or a collapsed membrane. A perimacular fold may form along the edge of the separation of the ILM from the neurosensory retina at the cyst margin.

Sub ILM hemorrhagic macular cysts are almost pathognomic to Terson's syndrome. Fourteen cases of retinal folds from shaken baby syndrome or consequent to direct head trauma were analyzed from various literature reports, each had intracranial hemorrhage and various forms of intraocular hemorrhage, including HMC. The HMC's occur not only in traumatically induced cases of Terson's syndrome but also in patients with spontaneous subarachnoid hemorrhage. Accordingly, it has been proposed that intracranial hemorrhage, from whatever source, is the common denominator in the formation of both HMC's and their accompanying perimacular folds.

In the series originally presented at the Annual Meeting of the American Academy of Ophthalmology in 1990, it was found that of 25 eyes undergoing vitrectomy for Terson's syndrome, 8 (32%) demonstrated HMC's (Morris, R., Kuhn, F., Witherspoon, C. D., "Hemorrhagic Macular Cysts in Terson's Syndrome and its Implications for Macular Surgery," *Developments in Opthalmology* (1997) 29:44). After careful clinical examinations and light or electron microscopic evaluations, it was concluded that the ILM had formed the anterior cyst wall in five eyes. While several literature reports have characterized these hemorrhagic lesions as being subvitreous or under a proliferative membrane, it is believed by Morris et al. (see above) that the majority of hemorrhagic macular cysts in Terson's syndrome are in fact submembranous (beneath the ILM) rather than subvitreous (preretinal).

Although rare, submembranous HMC's in Terson's syndrome are the most frequent lesion in which the macular ILM is spontaneously lifted from the underlying neurosensory retina as a result of a disease process. Thus, it was postulated that if the denuded macula retains good function without reparative surface proliferation developing, similar non-traumatic surgical removal of the ILM during vitrectomy in certain cases of traction maculopathy might be endorsed. (Morris, R., Kuhn, F., Witherspoon, C. D., "Retinal folds and hemorrhagic macular cysts in Terson's syndrome," *Ophthalmology* (1994) 101:1). For example, in none of the five Terson's eyes in a series evaluated by the inventor and colleagues did reparative proliferation develop during an average follow up of 32 months (range: 6–70 months), and all adult eyes reached and maintained excellent 20/25 visual acuity.

Therefore, the desirability of developing procedures for the atraumatic surgical removal of the macular ILM in certain forms of traction maculopathy was suggested. ("Hemorrhagic Macular Cysts in Terson's Syndrome and its Implications for Macular Surgery," *Developments in Ophthalmology* (1997) 29:44). Even minimal ILM surface traction has been increasingly implicated in many forms of maculopathy and often the EMP/ILM layers become, in effect, fused together, not allowing surgical removal of EMP alone. Additionally, long-term macular function appears to be stable or improved even without the ILM. ("Hemorrhagic Macular Cysts in Terson's Syndrome and its Implications for Macular Surgery," *Developments in Ophthalmology* (1997) 29:44). Thus, ILM removal is an important technique in the treatment of all forms of traction maculopathy because only the removal of the ILM with all cellular and membrane proliferation on its surface ensures total relief from all traction on the underlying nerve fibers at the center of vision. However, the methods thus far developed for such ILM removal have certain deficiencies. The method of mechanical pulling tearing away the macular ILM with forceps can cause severe trauma to the macula and the resultant injury can cause ocular damage of equal severity to the problem the surgery is meant to correct.

The current method employed for removal of both EMP and the macular ILM consists of cutting and then grasping, or directly grasping, the macular EMP/ILM with specially designed micro-forceps, 1 mm in maximum diameter, and slowly pulling it apart from the neural retina. This is done with great care in order to avoid engaging the neurosensory retina.

One problem with the current method of tearing and peeling away the macular ILM is the physical trauma associated with pulling on the ILM until it separates thereby unavoidably stressing the underlying nerve tissue, sometimes causing irreparable nerve damage with worsened vision than may have been present preoperatively. Accordingly, the surgeon may proceed slowly and carefully but if too slowly the retina may be injured from light toxicity coming from the fiberoptic probe inside the eyeball enabling the surgeon's view. If the surgeon grasps too shallow then his movements are ineffectual, adding to the time of surgery and the chance of light toxicity. If the surgeon grasps too deep, permanent nerve damage and hemorrhage results. The difference is usually a matter of microns of forceps movement, causing the surgeon's mindset to be what has justly been described as "nerve-wracking." The mass of the forceps, although ever so small, often obscures the surgeon's view, further adding to the chance of surgical damage to the retina. As a result of the above factors, complete traction release is the exception rather than the rule. Finally, even in the unusual case of complete traction release, the nerve tissue will usually require several months to resume a smooth contour with best vision returning. Thus, for some twenty years, the removal of epimacular proliferation so as to restore central vision in the eyes that are approaching legal blindness has remained a vexing problem for vitreoretinal surgeons worldwide. The potential surgical risks and the uncertain benefits, as well as the high level of skill required to perform such surgery has caused many surgeons to be reluctant to intervene until vision is substantially lost. This has been true, despite the knowledge that persistence of EMP causes permanent destruction of nerve function at the center of vision, such that visual acuity is only partially restorable, and progressively less so, as the EMP is allowed to persist.

Solutions have been diligently sought over this twenty-year period, including progressively smaller and finer forceps. Finally, as an illustration of surgeons' frustration, in 1997, a new concept was introduced by Tano to surgically rub or scrape the surface of the retina at or near the macula with a flexible, rubber instrument upon which has been glued innumerable diamond chips so as to allow the device to purchase a hold on these barely visible membranes and/or ILM. This device was introduced and has been substantially used, despite the obvious risk of damage to the neural retina which underlays these thin membranes by rubbing or scraping the retinal surface with an intentionally roughened instrument, as well as the risk of diamond chips dislodging and permanently remaining on the retinal surface within the eye. These risks have been tolerated in the more or less desperate search for effective remedies for traction maculopathy because the device adds an additional means to gain a surgical edge against the all too frequent need to conclude the operation before achieving complete release of traction.

Wang U.S. Pat. No. 5,066,276, described injecting viscous material into the eye using a standard glue injector. Wang, however, did not apply this surgical procedure within the retina itself. Rather, Wang described injecting the viscous material between a glia cell membrane and the retina. Wang described his procedure as one in which the pressure applied to the retina is very diffuse and not localized in one small area in order to reduce stresses on the retina.

There remains a need for improved methods for removal of both epimacular proliferations and the abnormal ILM of the retina to completely relieve all forms of traction maculopathy in which the ILM is contributory. Such a method must be based upon minimizing surgical traction on the underlying nerve tissue at the center of vision (fovea). The method and apparatus described herein overcomes the above noted problems.

SUMMARY OF THE INVENTION

The present invention provides a novel method for performing surgery inside the human retina using fluidic ILM separation (FILMS) and simultaneous retinal smoothing to overcome the disadvantages of the previously known methods.

Briefly, the present invention is directed to a method of separating the ILM layer of the retina from the neural layer of the retina in order to remove the macular internal limiting membrane and all EMP on its surface. The method comprises inserting a hollow microcannula, considerably smaller than any such cannula heretofore, which is shaped at its distal end to conform tangentially to the surface of the retina, between the retinal ILM and the neural retina. After the microcannula is inserted, a sterile fluid is injected at a pressure of about 25 mm Hg through the microcannula between the ILM layer of the retina and the neural layer of the retina. The fluid pressure lifts the macular internal limiting membrane layer away from the neural layer of the retina, separating it in the process of lifting away and allowing for its easy forceps removal from the eye without inflicting any physical trauma upon the neural retina. The lifted macular internal limiting membrane is removed by grasping the free-floating macular internal limiting membrane with forceps and extending the macular internal limiting membrane separation as distant from the fovea as desired before tearing circumferentially about the fovea and removing from the eye. The present invention allows for the removal of the macular internal limiting membrane without mechanically peeling or tearing it away from the fovea, so as to minimize foveal traction and the resultant physical trauma to the fovea. Moreover, the present invention simultaneously actively smoothes the underlying distorted and wrinkled neural retina by an intentional build-up of localized pressure within the confines of the developing FILMS cyst of which it is the posterior border. Thus, visual recovery, the ultimate surgical goal, is substantially accelerated as compared to the months needed for passive, spontaneous retinal smoothing after forceps traction removal. The preferred substance for use in practicing the invention and achieving complete removal of the macular internal limiting membrane is sodium hyaluronate (Healon®), as manufactured by Pharmacia & Upjohn Inc. or chondroitin sodium hyaluronate (Viscoat®) as manufactured by Alcon, Inc.

The present invention allows surgeons to operate, for the first time, inside the human retina (intraretinal) rather than above its surface. In so doing, it enables the surgeon to gently, predictably, and rapidly remove the ILM and all EMP adhered to the neural retina. The gentleness of the invented method eliminates risk of mechanical traction from pulling on the nerve fibers. The speed of the method, typically 4 minutes as opposed to 15 minutes, substantially reduces the risk of light toxicity. The predictability of the method allows for a more certain benefit from the surgery. Moreover, the method affords a significant decrease in the surgical skill level needed to treat traction maculopathy and makes visual recovery more rapid, more certain, and more complete. The sum effect is to enable patients suffering visual loss due to traction maculopathy of any type to seek and find earlier and more certain relief from distorted and reduced visual acuity, while the associated neural retinal abnormality is still reversible.

It is the principle object of the present invention to provide an improved method for macular ILM removal and retinal smoothing. Other objects and advantages of the present invention will become readily apparent from the following detailed description taken in conjunction with the accompanying drawings.

BRIEF DESCRIPTION OF THE DRAWINGS

A better understanding of the present invention will be had upon reference to the following detailed description when read in conjunction with the accompanying drawings.

DETAILED DESCRIPTION OF THE PREFERRED EMBODIMENTS

Definitions

"Maculorhexis" is the removal of the macular internal limiting membrane (ILM) by the production of a circular, 360° ILM tear concentric with the fovea, while minimizing foveal traction. This procedure is used to relieve all forms of traction maculopathy in which the ILM is contributory, as a result of its innate inelasticity or its action as a scaffold for fibrocellular proliferation (EMP).

"Traction Maculopathy" is a pathological dysfunction of the macula partially or entirely secondary to abnormal tangential or anteroposterior forces (e.g. macular hole, epeimacular proliferation, vitreomacular traction syndrome, diffuse diabetic macular edema, cellophane maculopathy).

"Fluid" is a substance whose molecules move easily across one another; a liquid or a gas.

"Neural Retina" is the middle layer of the retina, between the ILM and the pigment epithelial layers, which is composed of nerve tissue and which generates and transmits the electrical signals ultimately recognized as vision.

Preferred Embodiments

Figure 1:
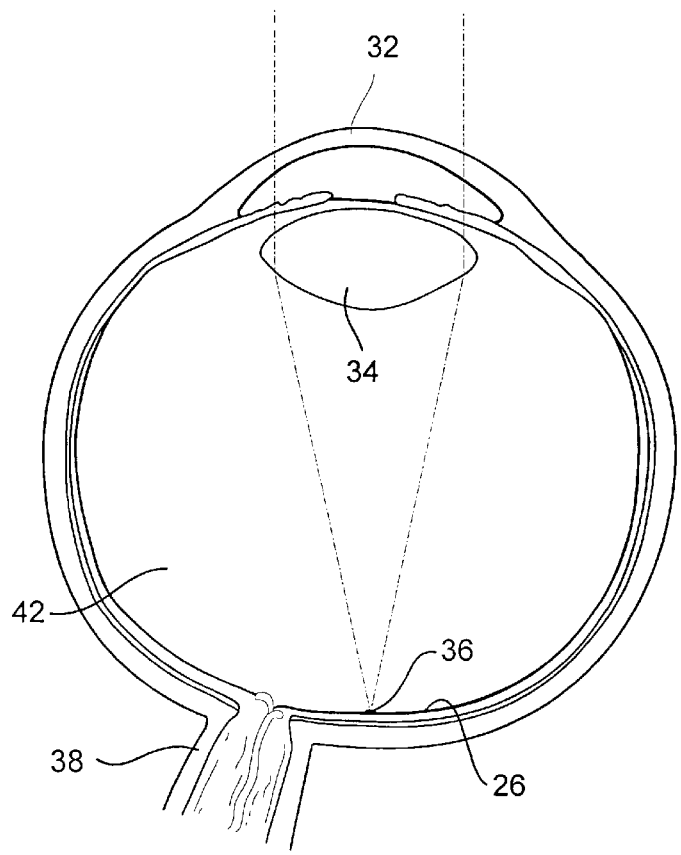
FIGS. 1 and 2, previously discussed, show the prior art.
Figure 2:
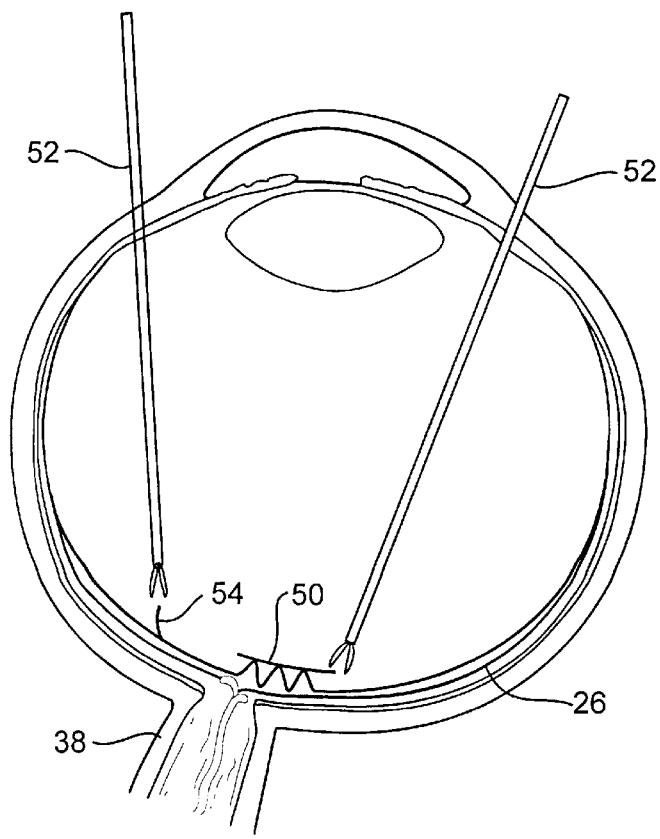
Figure 3:
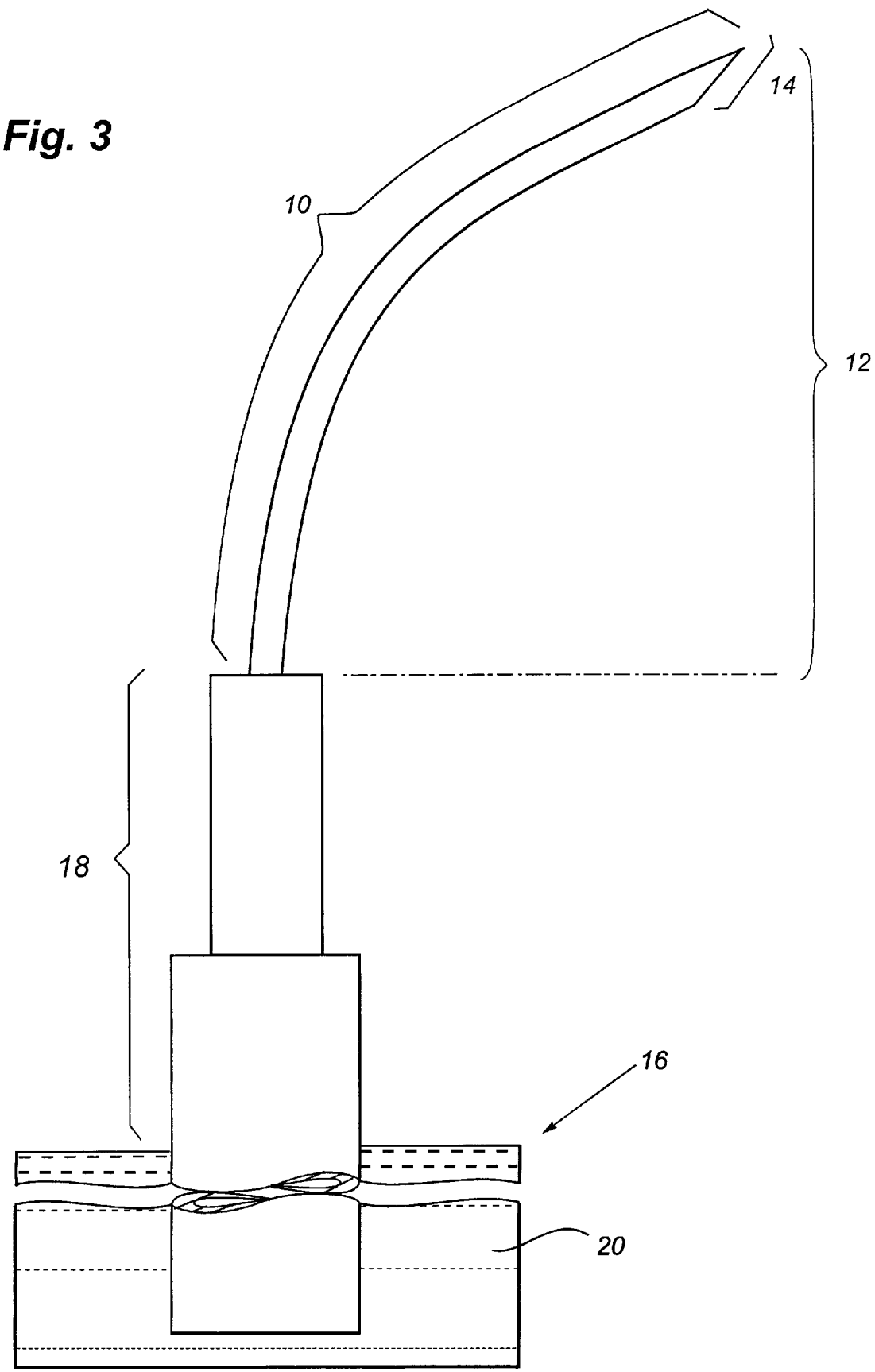
FIG. 3 is a representation of the microcannula apparatus to be used to perform the new method for fluidic ILM separation (FILMS).
Figure 4:
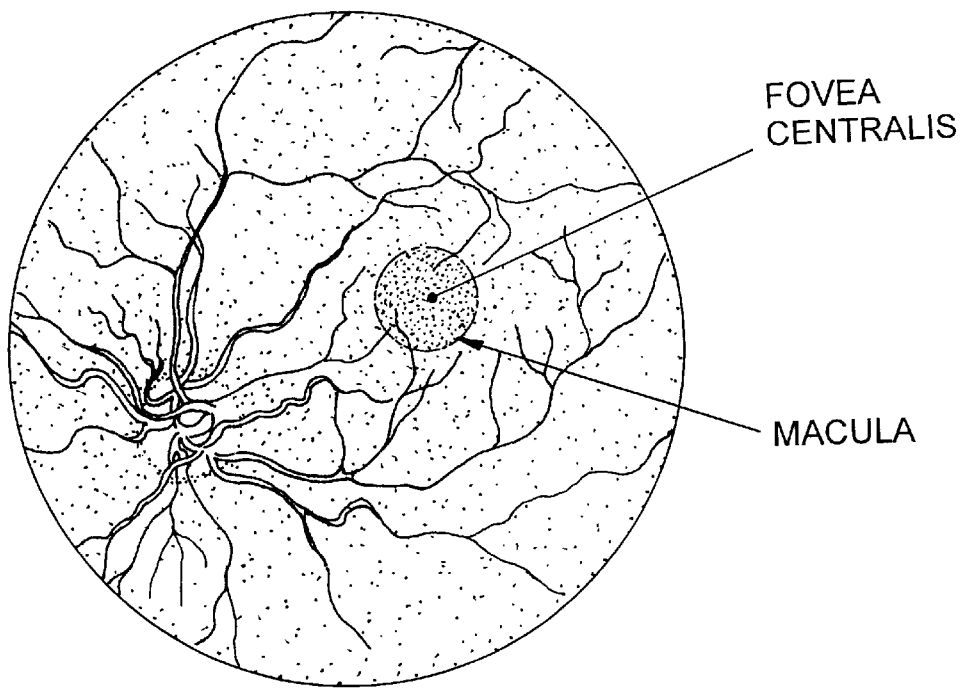
FIG. 4 is the interior of the posterior half of the left eye as viewed through an ophthalmoscope. The area of most acute vision, the macula, is shown with the fovea centralis at its center.
Figure 5:
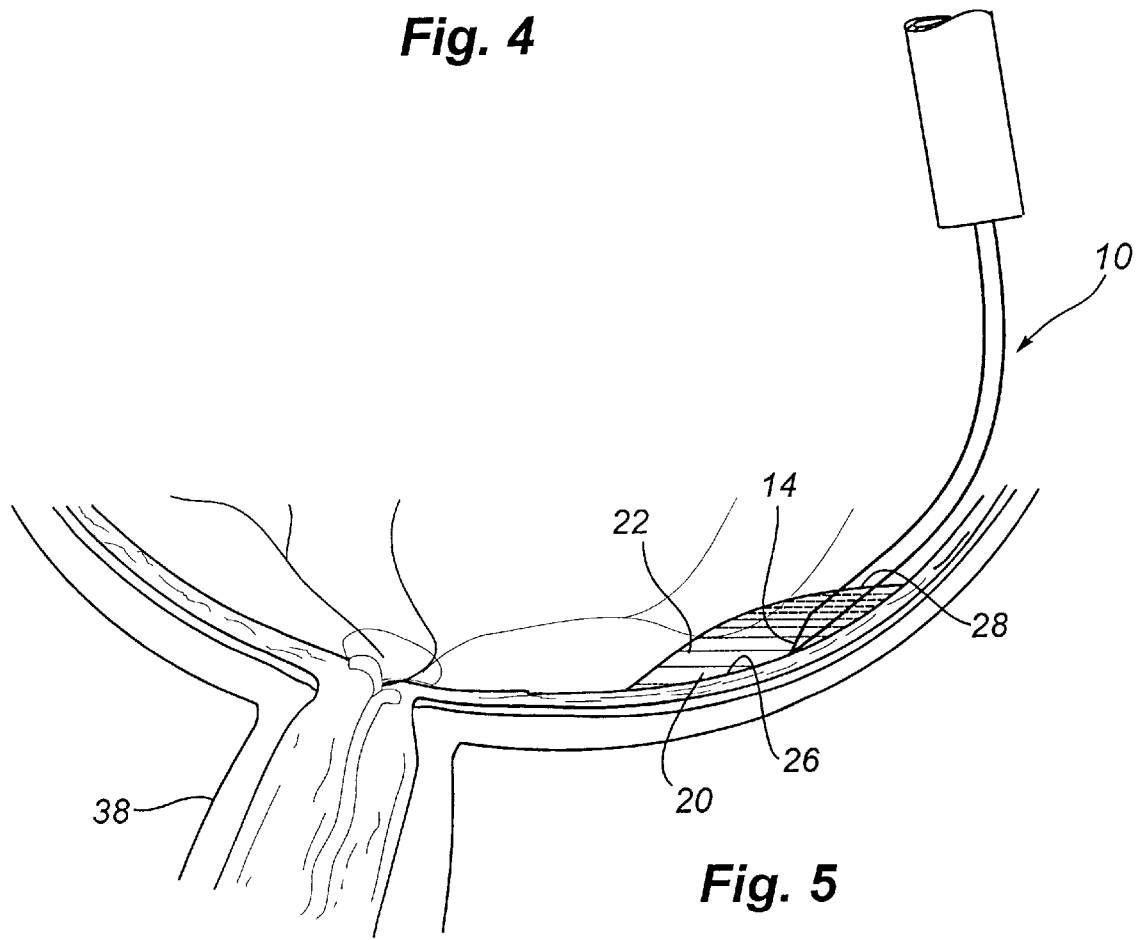
FIG. 5 is a cross-sectional view of the eye undergoing a macular FILMS procedure in accordance with the method of the present invention.

Disclosed herein is a novel procedure allowing surgery within the human retina to remove the internal limiting membrane utilizing fluidic separation. With reference to FIG. 4, to begin the process of ILM removal, an optimal starting point is chosen within the arcade vessels but remote from the fovea. Additionally, the chosen starting point site should not overlie the papillomacular bundle. Furthermore, the starting point is selected on the basis of the appearance of the ILM, and for surgical convenience. In a preferred embodiment, referring to FIG. 3, the specially designed hollow microcannula (microcannula and fluid injector) has a proximal end 18 and a distal end 12. The microcannula has an outside diameter of approximately 800 microns (0.8 mm)

at its proximal end 18 stepwise tapering to an outside diameter of approximately 100 microns (0.1 mm) at its distal end 12. The microcannula is shaped at its distal end 12 to conform tangentially 10 to the surface of the retina 26. The microcannula is beveled at the distal tip 14 to promote an effective entry through the macular ILM retinal layer 22 (FIG. 5) at the surface of the retina 26 and is adapted at the distal tip 14 to discharge a substance which is contained in a reservoir 16 attached to the microcannula of FIG. 3. The point of insertion 28 of the microcannula is at the surface of the retina 26 and through the macular ILM retinal layer 22. A sterile substance stored in the reservoir 16 attached to the microcannula is injected at a pressure of about 25 mm Hg through the microcannula so as to discharge from the distal tip 14 beneath the macular ILM 22 within the retinal tissue. The actual injection pressure is selected by the surgeon immediately prior to microcannula introduction into the eye, so that said injection pressure moves the injectate fluid through said FILMS microcannula at the desired rate of flow for effective but non-traumatic cleavage between the ILM and neural layers of the retina. The substance 20 then cleaves the human retina by lifting the macular ILM 22 away from the neural retina, allowing for its subsequent forceps removal without inflicting any physical trauma upon the neural retina due to adhesion of the macular ILM 22 to the surface of the neural retina. The separated macular ILM 22 is removed by grasping said macular ILM 22 with forceps and extending its separation by gentle traction beyond the macula, then tearing said macular ILM 22 in a circular, 360° fashion concentric with the fovea.

The preferred substance 20 to discharge from the distal tip of the microcannula 14 and achieve complete fluidic separation of the macular ILM 22 from the neural retina is a thick clear fluid such as sodium hyaluronate (Healon®) or chondroitin sodium hyaluronate (Viscoat®). These are preferred because their thickness helps form the FILMS cyst, lifting the macular ILM 22 and simultaneously smoothing the neural retina without detrimental leakage at the FILMS microcannula insertion site. Furthermore, sodium hyaluronate creates a clear field of vision thereby facilitating intra-operative inspection of the retina. However, it is possible that a different fluid, such as sterile saline, or a gas could be used.

The free-floating raised macular ILM 22 is then grasped by forceps. When the forceps are then used to grasp the macular ILM 22 separated from the surface of the retina 26, the maneuver becomes predictable and non-traumatic because there is no need to tear or peel the macular ILM 22 away from any direct adhesion to the fovea and surrounding macular surface of the retina 26, eliminating any vertical or tangential force vectors as placed upon the fovea by forceps ILM removal, substituting in its stead a very gentle and precisely controlled tamponad pressure. Then, a (smooth-edged continuous tear) "rhexis" is created by slowly tearing the ILM in a circular pattern concentric with the fovea, at a distance from the fovea as selected by the surgeon after further mechanical stripping of the ILM beyond the macular FILMS cyst. A surgeon can often create the complete 360° rhexis in one motion. However, if the tear is incomplete, the ILM is simply regrasped at the new edge, and the rhexis is resumed.

The problem of adhesion and the necessity to tear and peel the macular ILM from the surface of the retina (fovea and macular center of vision) and the resultant physical trauma impressed upon these areas is completely avoided. By injecting a fluid substance within the retina tissue, the macular ILM is separated from contact with the neural retina prior to grasping and removing it from the retina. Therefore, the macular ILM is never actually torn or peeled away from the retina and there is no physical trauma caused by adhesion of the macular ILM to the neural retina because the injected fluid lifts the membrane away from the surface of the retina before it is removed using the forceps.

While embodiments and applications of this invention have been here shown and described, it would be apparent to those skilled in the art that many more modifications are possible without departing from the inventive concepts herein. The invention, therefore, is not to be restricted except in the spirit of the appended claims.

EXAMPLES

It must be noted that as used herein and in the appended claims, the singular forms "a" "and" and "the" include the plural references unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are fully incorporated herein by reference.

What is claimed is:

1. A method for performing surgery inside a human retina using fluidic internal limiting membrane separation comprising:

inserting a hollow microcannula between a neural retina and a retinal internal limiting membrane at or near a macula;

injecting a sterile fluid substance through said microcannula between a neural retina and a retinal internal limiting membrane, thereby cleaving a retina and lifting a separated macular internal limiting membrane away from a surface of the neural retina, simultaneously, by active, localized pressure, causing a distorted neural retina to resume its natural smooth contour; and removing a macular internal limiting membrane along with substantially all epimacular proliferation or vitreomacular traction.

2. The method of claim 1, wherein said sterile substance is sodium hyaluronate.

3. The method of claim 1, wherein said sterile substance is injected with or without a dye.

4. The method of claim 1, wherein said hollow microcannula has a distal end and a proximal end, and said microcannula is shaped at its distal end to conform tangentially to the surface of a retina near a macula while inserted from an eye wall entry site at the pars plana, and is adapted at the distal tip to discharge said sterile substance from the distal tip of the microcannula, and to allow easy entry through an internal limiting membrane of a retina and optimal occlusion of the microcannula lumen by an overlying internal limiting membrane when minimally introduced, and in which said microcannula is so microscopic as to not substantially injure a neural retina when introduced under an ILM.

5. The method of claim 1, wherein said sterile substance is an isotonic saline solution.

6. The method of claim 1, wherein said sterile substance is a gas.

* * * * *